United States Patent [19]

Smith

[11] 4,122,853
[45] Oct. 31, 1978

[54] INFRARED LASER PHOTOCAUTERY DEVICE

[75] Inventor: Michael R. Smith, Thousand Oaks, Calif.

[73] Assignee: Spectra-Med, Thousand Oaks, Calif.

[21] Appl. No.: 777,390

[22] Filed: Mar. 14, 1977

[51] Int. Cl.$^2$ ............................................. A61B 17/36
[52] U.S. Cl. ................................. 128/303.1; 128/276
[58] Field of Search ....................... 128/303.1, 395, 276

[56] References Cited

U.S. PATENT DOCUMENTS

| 3,693,623 | 9/1972 | Harte et al. | 128/303.1 |
| 3,892,541 | 9/1976 | L'Esperance | 128/303.1 |

FOREIGN PATENT DOCUMENTS

| 2,309,205 | 10/1973 | Fed. Rep. of Germany | 128/303.1 |
| 2,511,248 | 4/1975 | Fed. Rep. of Germany | 128/303.1 |
| 447,894 | 6/1975 | U.S.S.R. | 128/303.1 |

*Primary Examiner*—Lawrence W. Trapp
*Attorney, Agent, or Firm*—Warren T. Jessup

[57] ABSTRACT

An apparatus and method for cauterizing biological tissue while providing isolation from surrounding absorbing tissue and fluid media. The device is comprised of a probe having a special window through which an infrared laser beam is directed to cauterize the biological tissue. The device is comprised of an infrared laser beam generator, a control circuit for controlling the intensity and duration of the laser beam and an articulated arm for directing the laser beam to the probe. The probe is comprised of a hollow, laser light guide tube having an infrared transparent window in its tip which permits the tip to be brought into contact with biological tissue such as vascular tissue to be cauterized while excluding the surrounding absorbing tissue from the effects of the beam. The probe may also include an adjacent endoscopic viewing tube and accessory tube to provide fluid, suction and optical illumination at the vicinity of the window.

21 Claims, 11 Drawing Figures

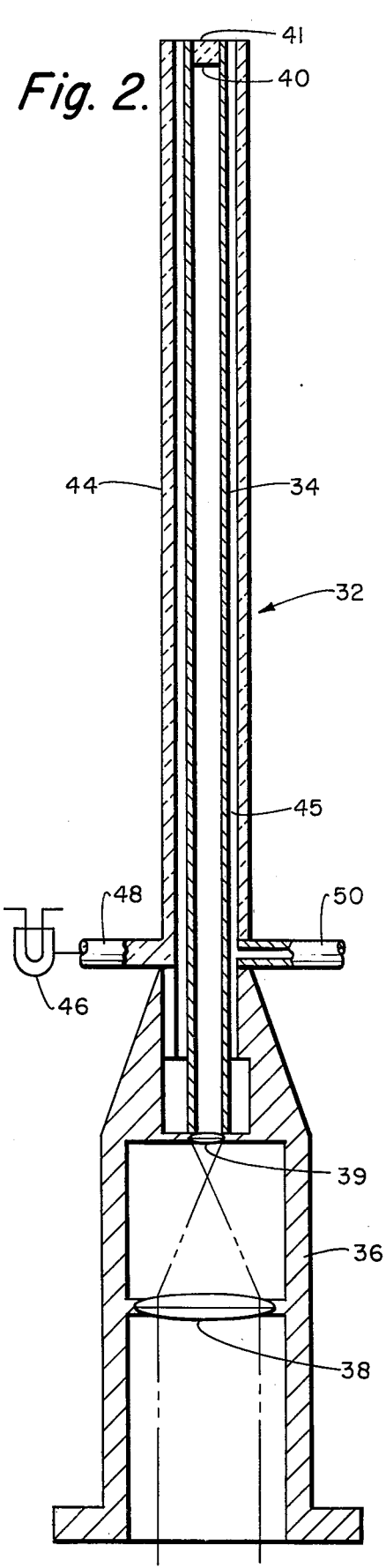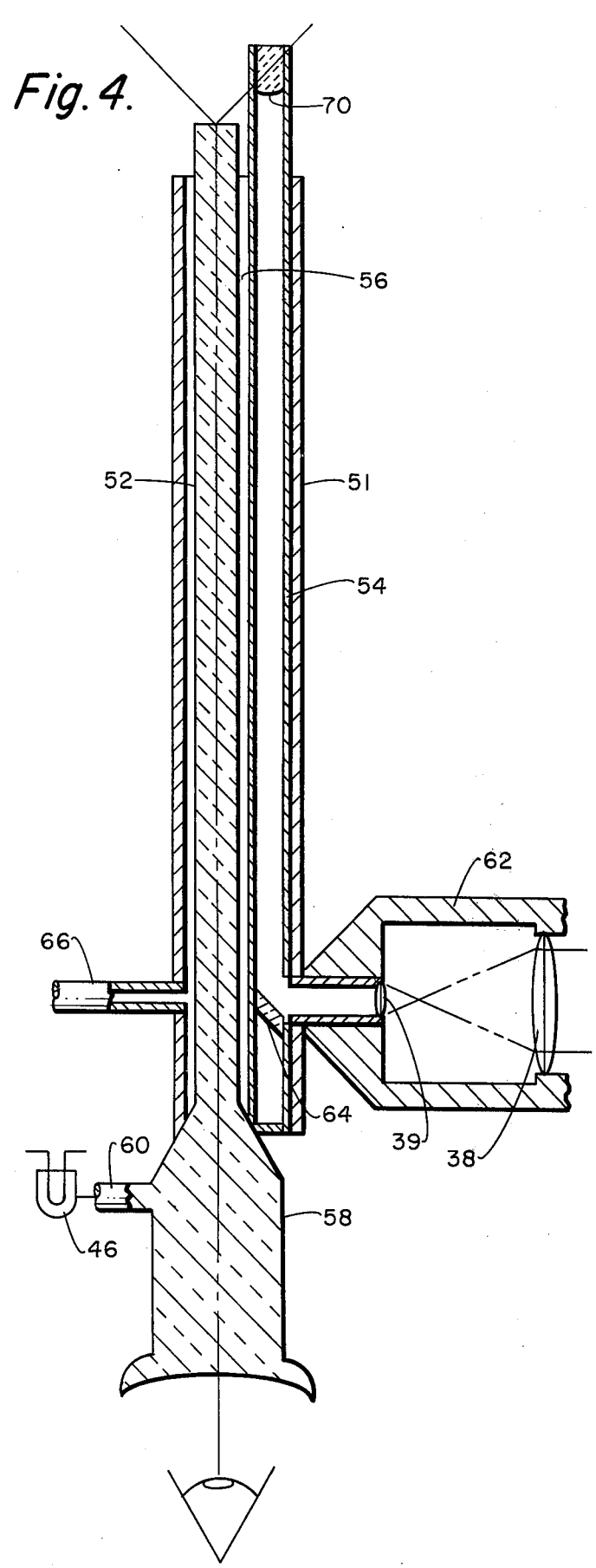

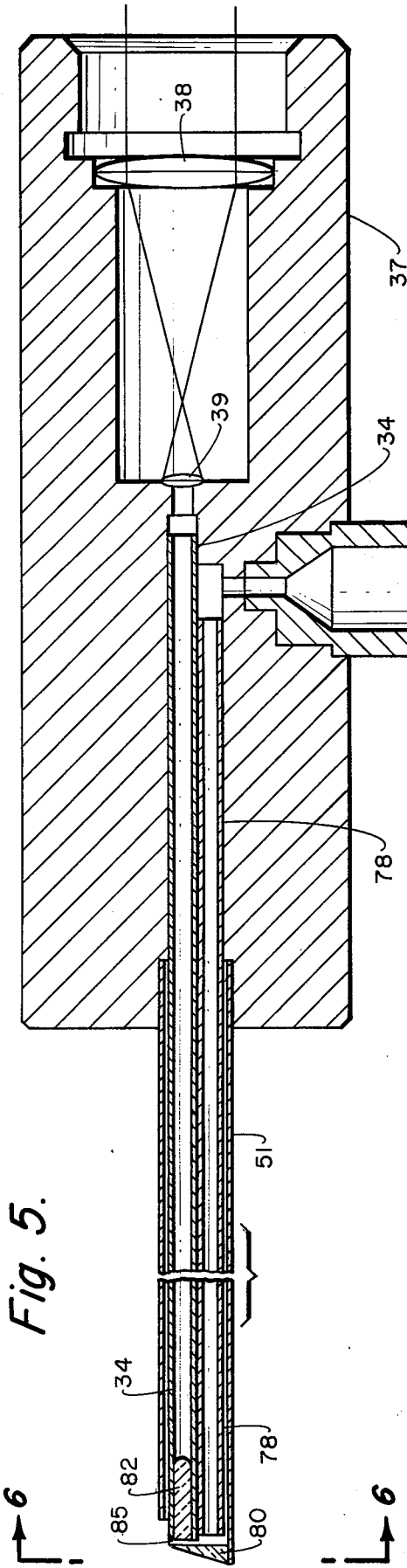
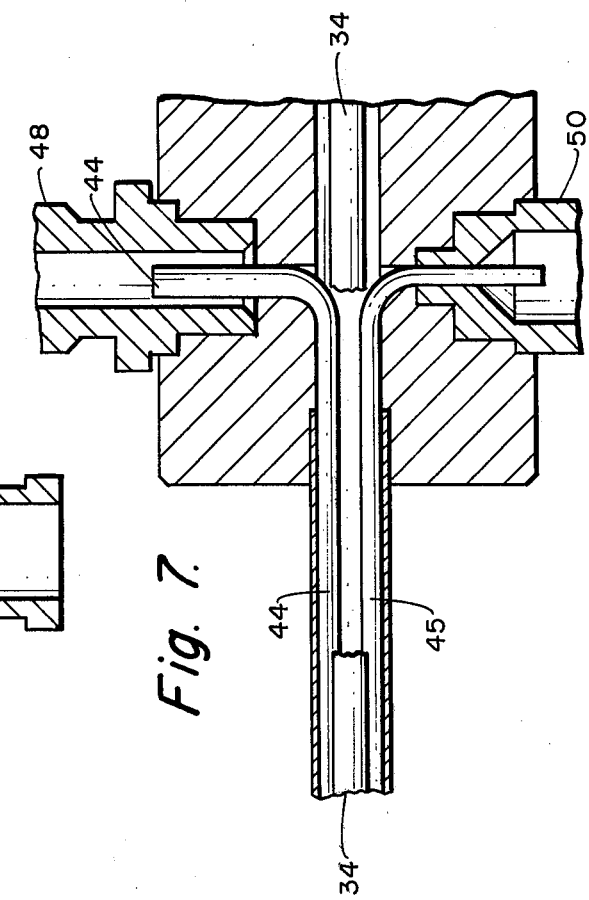
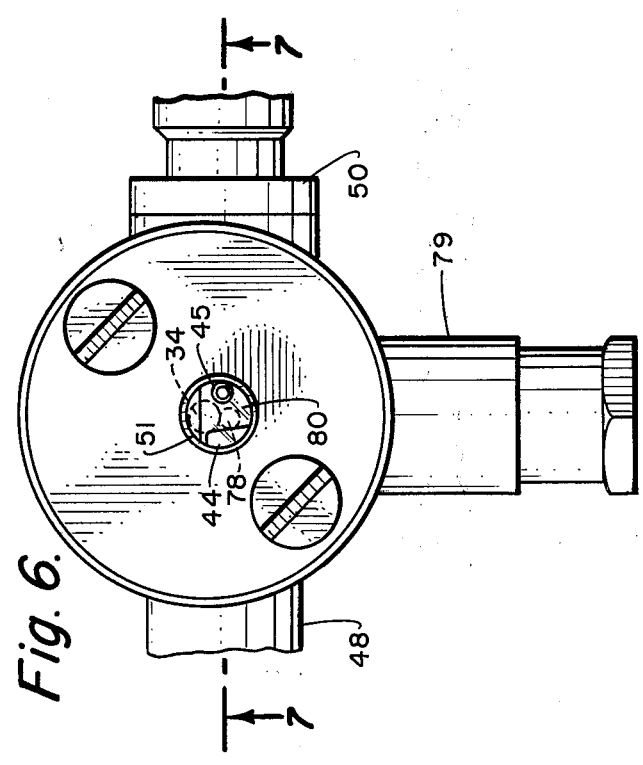

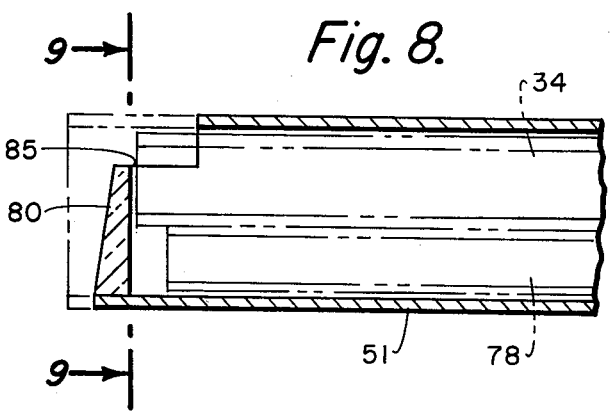
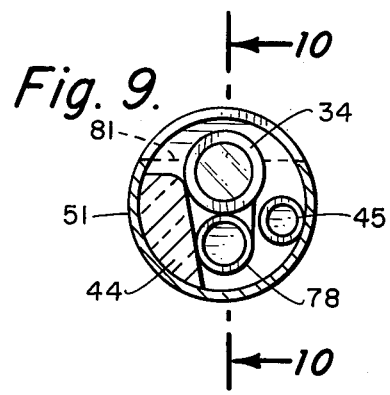
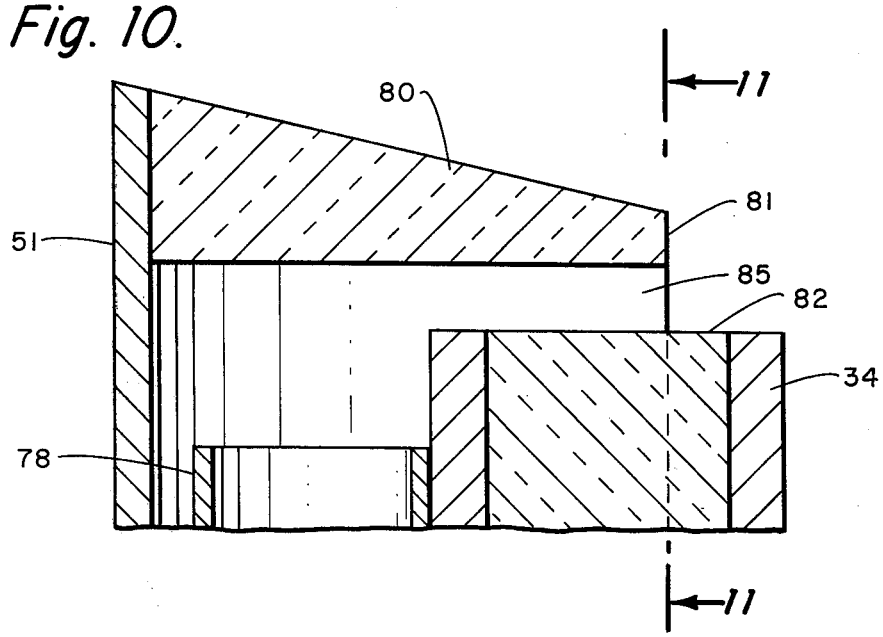
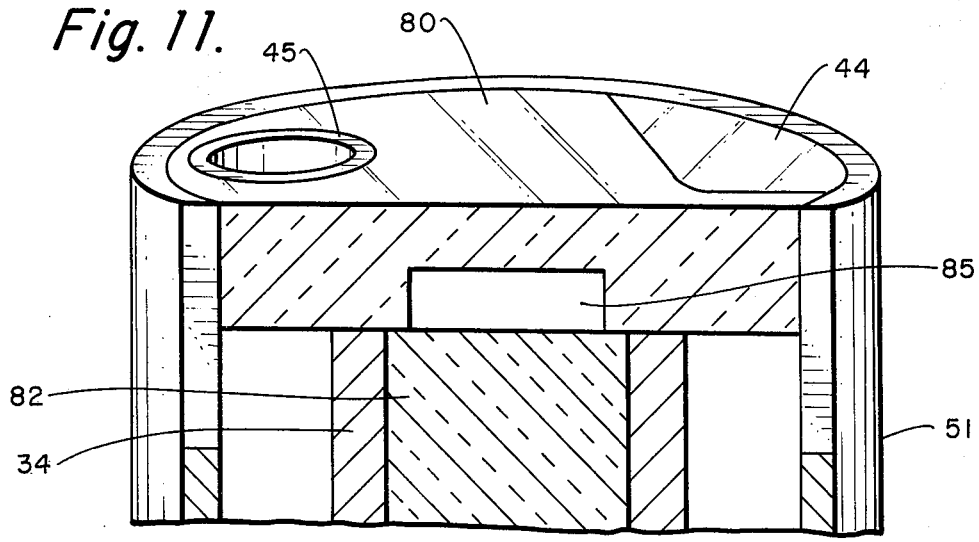

INFRARED LASER PHOTOCAUTERY DEVICE

BACKGROUND OF THE INVENTION

This invention relates generally to laser beam technology used in surgical procedures, and more particularly relates to the use of an infrared laser beam for delivery of energy to a localized area within an absorptive medium.

The use of laser beams as a tool for performing various surgical procedures, such as cutting and cauterizing various types of biological tissues, is well known in the art. The cutting action is provided by an intense local heating of the tissue due to absorption by the tissue of the laser energy in the focused laser spot. Such devices have been used previously for various surgical procedures such as dermatological port wine birthmark removal, laryngological and gynecological polyp excision and opthalmic retinal photocoagulation. One such prior art device utilizes a carbon dioxide infrared laser beam which is movably positioned by a directional mirror and focused by a lens through an intervening air interface to concentrate the laser energy and the tissue surface of a remote treatment site.

All of the prior art utilizing carbon dioxide infrared laser beam tissue treatment has been limited to the treatment of surface tissues which can be approached through an adjacent air interface. The use of this particular range of laser wave lengths for the treatment of biological tissue situated within an intervening or surrounding absorbing medium has been precluded in the prior art because the $CO_2$ laser radiation is completely absorbed by the outer layers of fluid or tissue and the beam cannot penetrate into the underlying layers of tissue without vaporizing or damaging the outer layers. In many instances (e.g. gastric surgery, intraocular surgery, and neurosurgery) it is desirable to operate within an internal region and to localize placement of the laser energy within a highly absorptive medium without damaging the intervening and surrounding tissue. For example, if retinal vascular tissue were to be cauterized intraocularly be means of an infrared laser beam, or similarly if a bleeding gastric ulcer were to be cauterized in situ while surrounded by normal gastric fluids, these sites would lie within an absorptive medium. Previous devices utilizing this type of infrared laser beam could not be used to selectively treat tissue which was immersed within a surrounding absorptive medium, without being absorbed by the intervening tissue.

SUMMARY OF THE INVENTION

The purpose of the present invention is to provide an infrared laser beam, such as a carbon dioxide laser for use in photocoagulation or localized surgical procedures within an absorptive medium.

The present invention provides a device for receiving an infrared laser beam, for manipulating, focusing and delivering the focused laser energy to a predetermined localized area within an absorptive medium while isolating the surrounding medium from damage by absorption of the laser energy.

The invention is particularly useful for performing infrared surgery of tissue which is immersed and surrounded by other water-bearing material, or absorptive material, such as the vitreous medium of the eye.

The system is comprised of a $CO_2$ laser beam generator and a control system for controlling the intensity and duration of the beam. The laser beam is directed in a flexible manner from the laser to a probe by means of an articulated arm light guide for treatment of a localized area. The probe is comprised of a highly polished laser light guide tube by which the laser energy can be selectively delivered to a particular area while isolating the surrounding absorptive medium from damage by the laser energy. The probe can be passed through a water-bearing biological tissue and brought directly into contact with the area to be treated. The laser energy emerges through the outer surface of a tiny transparent window in the tip of the probe. Thus, the device can be effectively used to cauterize vascular tissues such as those found in the eye or selectively treat other tissue immersed within a surrounding absorptive medium.

It is one object of the present invention to provide an infrared laser beam for use in treating localized areas within an absorptive medium.

Another object of the present invention is to provide an infrared laser beam surgical tube which can be used for photocauterizing intraocular vascular tissue.

Other objects, advantages and novel features of the invention will become apparent from the following detailed description of the invention when considered in conjunction with the accompanying drawings, wherein like reference numbers identify like parts throughout.

BRIEF DESCRIPTION OF THE DRAWINGS

FIG. 2 is a sectional view of a probe for use with the photocautery system of FIG. 1.

FIG. 4 illustrates another embodiment of a probe for use in the photocautery system of FIG. 1.

FIG. 5 is a sectional view of an alternate embodiment of the probe for performing intraocular vitrectomies.

FIG. 6 is an end view of the embodiment illustrated in FIG. 5.

FIG. 7 is a partial section view of the vitrectomy probe taken at 7—7 of FIG. 6.

FIG. 8 is a partial section of the probe tip.

FIG. 9 is a sectional view taken at 9—9 of FIG. 8.

FIG. 10 is an enlarged partial section of the immediate area of the tip.

FIG. 11 is an enlarged perspective view of the tip end illustrating the relationship of the components.

DETAILED DESCRIPTION OF THE PREFERRED EMBODIMENT

Figure 1:
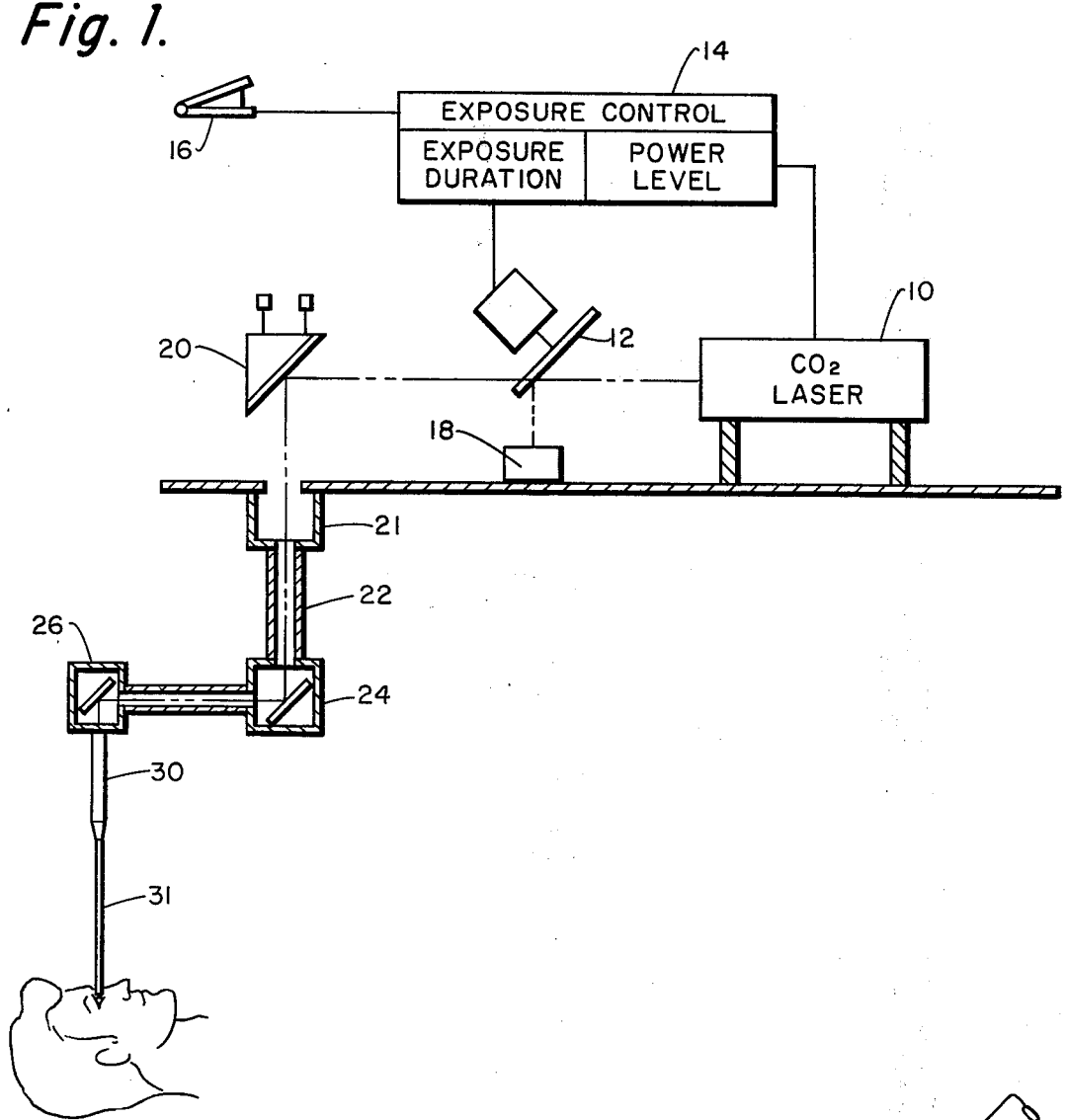
FIG. 1 is a semi-schematic drawing of the overall laser photocautery system of the invention.

Referring to FIG. 1, there is shown a laser photocautery system which is comprised of a $CO_2$ laser beam generator 10 for delivering a collimated infrared laser beam, a rotary shutter 12 which is controlled by control system 14 operated by a foot pedal switch 16. The control system 14 determines the intensity and duration of the laser beam energy on the area being treated. The rotary shutter 12 normally blocks the laser beam from the generator 10 and diverts it to a power meter 18, prior to exposure for treatment.

When the shutter 12 is open, the beam is deflected by a mirror 20 into the near end of an articulated arm 22. The mirror 20 provides alignment of the infrared laser beam with the access of the first segment of articulated arm 22. Rotatable mirror joints 21, 24 and 26 on the successive articulated arm segments provide 6° of freedom of motion to movably control the position of the laser beam as it emerges from the output of the articulated arm while maintaining angular alignment with respect to the optical axis. The beam is flexibly delivered through the articulated arm to a probe 30 for treatment of a localized area. In this case treatment of the eye is being illustrated, but the device could be used for treatment of any region within an intervening absorptive medium.

One embodiment probe 32 is illustrated in FIG. 2. In this probe a laser light guide tube 34 is attached to a probe body 36 which contains a beam-contracting telescope comprised of lenses 38 and 39. The laser light guide tube 34 is a highly polished metallic tube whose inside surface reflects the infrared laser radiation. Approximately 90% of a $CO_2$ laser beam radiation can be transmitted through a one millimeter inside diameter tube 90 millimeters long.

In order to bring the laser beam and the laser light guide tube directly to the site to be treated, a window 40 is provided in the tip of the tube. This prevents any intervening water-bearing biological tissue from entering the laser light guide tube 34 and allows the tip 41 of the laser light guide tube to make direct contact with the area to be treated.

In order to illuminate the area being treated for external microscopic viewing, an annular light conduit 44 comprised of a fiber optic bundle is mounted adjacent with the laser light guide tube. The annular gap 45 provides a passageway for irrigation during treatment. During an operative procedure a source 46 illuminates the treatment area by directing the light into the light conduit by means of light coupling connector 48. To irrigate the area being treated with saline solution, a tube 50 would connect and provide a flow of a fluid through passageway 45 to the vicinity of the tip of the probe 32.

An alternative construction for the probe is illustrated in FIG. 4. This embodiment has all the features of the previous embodiment, except that it incorporates an endoscope for direct viewing of the area being treated. In this embodiment a case 51 encloses an endoscopic viewing device 52, along with a laser light guide tube 54 and provides a passageway 56 for irrigating the area being treated as before. The endoscope has a microscope eye piece 58 for viewing the area being treated and includes a fiber optic coupler 60 to provide illumination for viewing through the endoscope. In this case the laser beam is directed through a probe body 62 having the beam contracting telescope composed of lenses 38 and 39 directing the beam into the laser light guide tube 54 by reflection from a mirror 64. Tube 66 connects a fluid to passageway 56 for irrigating the treated area as before.

The end of the laser light guide tube 54 has a window 70 as before to enable access to the area being treated with the infrared laser beam while preventing absorption of the laser energy in the intervening tissue. In this embodiment the window has a curved inner surface for imparting optical power to the beam, i.e., the beam can be brought to a focused spot or line at the outer surface of the window due to the lensing effect of the curved inner surface of the window.

Figure 3:
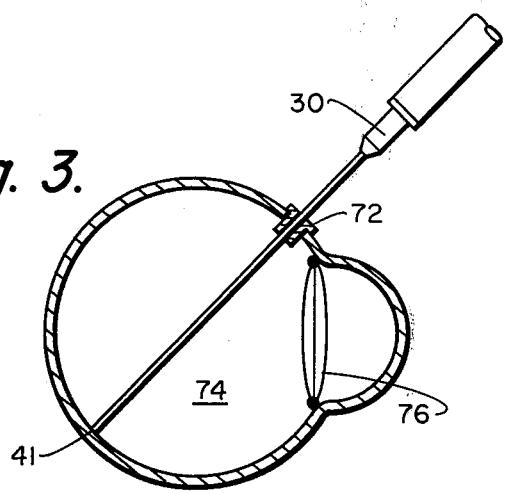
FIG. 3 illustrates the use of the photocautery system for cauterizing vascular tissue within the eye.

The use of the device in photocoagulation or cauterization of vascular tissue in the eye to prevent hemorrhaging is illustrated in FIG. 3. To cauterize a blood vessel in the posterior chamber of the eye, an incision is made in the pars plana region and a temporary cannula or collar 72 inserted to permit passage of the probe 30 into the vitreous chamber of the eye. The probe tip 41 is then inserted into the eye, passing through the vitreous humour 74 until the tip of the probe 30 contacts the vascular tissue to be cauterized. The surgeon then operates the foot pedal 16 (FIG 1) which exposes the vascular tissue to a predetermined intensity of the beam for a predetermined length of time.

The collimated infrared laser beam enters the large end 36 of the photocautery probe body and is reduced in diameter by the beam-contracting telescope. The beam is recollimated after passing through second lens 39 and enters on axis into the hollow laser light guide tube 34. The diameter of the small beam measured to the $1/e^2$ intensity level of the beam profile should be approximately equal to 0.64 times the diameter of the laser light guide tube for efficient coupling. A typical diameter of the large laser beam entering the probe body is 6 millimeters measured to the $1/e^2$ diameter.

The beam-reducing telescope may be comprised of a 38 millimeter focal length zinc selenide (ZnSe) positive meniscus lens separated by 41.8 millimeters from a 3.8mm focal length ZnSe positive miniscus lens providing a beam reduction of ten times from 6mm to 0.6mm. This diameter couples efficiently into the 1mm inside diameter of the hollow laser light guide tube 34.

After passing through the laser light guide tube, the beam emerges through the window 40 and is absorbed by the tissue or other absorbing material contacted by or immediately adjacent to the outside surface of the window. The window 40 is composed of a material such as ZnSe which transmits the infrared radiation with negligible absorption and is heremetically sealed into the tip 41 of the laser light guide tube. The window 40 may be a plain parallel cylindrical optical element and should be highly polished and anti-reflection coated to permit unattenuated passage of the laser beam into the medium adjacent to the outside window surface. A flat window will provide an emergent laser beam having a diameter slightly smaller than the 1 millimeter laser light guide tube diameter with a beam profile similar to the profile of the small diameter beam entering the laser light guide tube.

If desired, optical power may be imparted to the window by curving the inner surface of the window. With a proper spherical curvature on the inner surface of the window, the beam will be focused to a small spot on the window outer surface. Likewise, with a proper cylindrical curvature, the beam will be brought to a line focus at the outer surface of the window. The spot and the line focus cause the laser energy to be concentrated by increasing the flux density $W/cm^2$. An important function of the window 40 is to permit the infrared laser beam to pass through a laser light guide tube into the immediate surrounding medium, such as water or a water-bearing biological tissue, while hermetically sealing and isolating the interior of the laser light guide tube from the surrounding absorptive medium.

An alternate embodiment of the invention which can be used for performing intraocular victrectomy and ocular lensectomy is illustrated in FIGS. 5 through 11. In this probe embodiment, a probe body 37 and a case 51, attached thereto, encloses an illuminating light conduit 44, a laser light guide tube 34, and has a passageway 45 for passing irrigating fluid to the vicinity of the probe tip shield 80. An additional passageway 78 is provided to act or be used as a suction tube.

Fluid inflow for irrigating the area is provided by a fluid delivered through connector 50, connecting fluid passageway tube 45 to a fluid source (not shown) for replacing the volume of vitreous tissue removed through the suction tube 78. Visible illumination for viewing the vitrectomy site is provided through the light conduit 44 adjacent to the laser light guide tube 34 and suction tube 78. The light conduit 44 protrudes into the surface of the shield tip 80 providing direct illumination of the area of the intraocular vitrectomy.

FIGS. 8 – 11 illustrate the details of the vitrectomy probe tip construction. The tip shield 80 terminates at the point 81 covering a substantial portion of the light guide tube window 82, as can be seen in FIGS. 9 and 10. The tip shield 80 also surrounds the light conduit 44 and the fluid conduit 45 providing illumination and irrigation to the area being treated outside the vitrectomy probe. The tissue passageway 85 can be seen in FIG. 11 as a slot in the end of the tip shield 80 providing a gap between the light guide tube, window 82, and the shield 80. The suction tube 78 terminates at a point somewhat below the light guide tube 34 as can clearly be seen in FIG. 10. Thus, tissue can be drawn into the passageway 85 for cutting by the laser beam coming from window 82 and concentrated in the passageway between the window 82 and the tip shield 80. The cut tissue is then drawn into the suction tube 78 and out of the probe.

In operation for performing an intraocular victrectomy, a suction device or pump (not shown) is attached to a suction coupling connector 79 and vitreous tissue pulled through opening of a tissue passageway 85 adjacent to the tip shield 80. The narrow channel of the tissue passageway 85 confines the vitreous tissue to the area across and adjacent to the surface of the beam concentrating laser window 82. The inner surface of the window 82 is cylindrically curved to produce a line focus laser beam at the surface of the window. The high flux density at the line focus produces a cutting action to resect or remove the vitreous tissue within the confines of the tissue passageway 85. The severed tissue is consequently pulled into suction tube 78, through the probe body 90 and out through the suction coupling connector to a suitable receptacle.

If the surrounding medium is water or water-bearing biological tissue, the 10.6 micrometer wavelength $CO_2$ laser beam will be totally absorbed within approximately 100 micrometers from the outer surface of the window. The absorption coefficient for $CO_2$ laser radiation in water is $1 \times 10^3 cm^{-1}$ which means that the radiation is attenuated to 37% of the initial value after traversing a distance of only ten micrometers. Thus, the absorption of $CO_2$ laser radiation may be extremely well localized within an aqueous medium. The irrigation tubing illustrated in the embodiments of FIGS. 2 and 4 may be used to provide a flow of fluid, such as a saline solution, to the vicinity of the probe tip 41. Maintaining fluid in the vicinity of the window helps to prevent tissue from adhering to the outside window surface during photocautery of biological tissues.

The visible light conduit may be an annular fiber optic bundle for transmitting visible light from an illuminating lamp 46 to provide trans-illumination for viewing in the vicinity of the window. As in FIG. 4, the light conduit may be incorporated into an endoscope to provide intraocular viewing. A mirror (not shown) may be provided at the end of the endoscope to provide a view of the tip 41 and the window 40.

Thus, there has been disclosed a device for utilizing infrared laser beams for cauterizing or removing of biological tissue in situ while surrounded by an absorptive medium.

Obviously, many modifications and variations of the present invention are possible in light of the above teachings. It is therefore to be understood that the full scope of the invention is not limited to the details described herein and may be practiced otherwise than as specifically described.

What is claimed is:

1. An apparatus for treating by cauterizing or cutting blood vessels and other biological tissue comprising:
   laser beam generating means for generating a tissue absorbent laser beam;
   optical means for manipulating, focusing and delivering the laser beam to a desired location in an absorptive medium while isolating the surrounding and intervening medium from the beam, said optical means including;
   a laser light guide means,
   window means transparent to said laser beam sealing said laser light guide means,
   automatic control means for controlling the intensity and duration of said laser beam.

2. The apparatus according to claim 1 wherein said laser beam generating means comprises a carbon dioxide laser beam generator.

3. The apparatus according to claim 1 wherein said optical means further includes:
   a probe body; and
   a contracting beam telescope for reducing the beam diameter in said body.

4. The apparatus according to claim 3 wherein said transparent window is comprised of zinc selenide.

5. The apparatus according to claim 4 wherein said window is a plane parallel cylindrical optical element hermetically sealed in the end of the light tube.

6. The apparatus according to claim 5 wherein said window is constructed to concentrate the laser beam at the outer surface of the window.

7. The apparatus according to claim 6 wherein said window is constructed to provide a spot focus.

8. The apparatus according to claim 6 wherein said window is constructed to provide a line focus.

9. The apparatus according to claim 1 including:
   an endoscope conjoining said probe whereby the area being treated may be viewed.

10. The apparatus according to claim 4 including:
    a passageway conjoining said light guide tube; and
    means for delivering a fluid through said passageway whereby the area being treated may be irrigated.

11. The apparatus according to claim 10 including:
    means for viewing the area being treated.

12. The apparatus according to claim 11 wherein:
    said viewing means comprises an endoscope; and
    said passageway is circumjacent said endoscope.

13. The apparatus according to claim 12 including:
    means for illuminating the treatment area.

14. The apparatus according to claim 13 wherein:
    said illuminating means includes a fiber optic bundle concentric with said laser light guide tube; and
    said passageway being between said concentric fiber optic bundle and said laser light guide tube.

15. A method of treating by cauterizing or cutting vascular or other biological tissue comprising:
    passing a hollow laser light conducting probe through an absorbing medium to the area of the tissue to be treated;
    isolating the surrounding area of tissue by sealing the tip of the probe with a window capable of passing the infrared laser beam with a minimum of attenuation;

contacting the tissue to be treated with the tip of the probe;

generating a laser beam in the infrared region of predetermined intensity for a predetermined duration;

directing said beam through said probe to said tissue whereby said tissue may be treated.

16. An apparatus for removing vitreous tissue comprising:

laser beam generating means for generating a tissue-absorbent laser beam;

optical means for manipulating focusing, and delivering the laser beam to a desired location in an absorptive media while isolating the surrounding and intervening medium from said beam;

automatic control means for controlling the intensity and duration of said laser beam;

a suction passageway adjacent to said optical means;

a focusing tip on said optical means for focusing said laser beam in the area of the end of said suction passageway;

a window transparent to said laser beam in said focusing tip for focusing said laser beam to a line;

whereby said laser beam severs vitreous tissue drawn into said suction passageway for removal of said tissue.

17. The apparatus according to claim 16 including:

a fluid passageway parallel and adjacent to said suction passageway for delivering a fluid to replace the volume of tissue drawn out through said suction passageway.

18. The apparatus according to claim 16 including:

an illuminating light conduit parallel and adjacent to said optical means for illuminating and viewing the area surrounding said focusing tip.

19. The apparatus according to claim 16 wherein said optical means comprises:

a probe body;

a contracting beam telescope for reducing the beam diameter in said body;

a hollow laser light guide tube receiving the narrowed beam from said body; and transparent window means transparent to said laser beam sealing laser light guide tube.

20. The apparatus according to claim 19 wherein said focusing tip comprises:

line focusing means for focusing said laser beam into a line.

21. The apparatus according to claim 20 wherein said line focusing means comprises a cylindrical curvature on the internal end of said transparent window.

* * * * *